United States Patent [19]

Furie et al.

[11] Patent Number: 4,783,330
[45] Date of Patent: Nov. 8, 1988

[54] MONOCLONAL ANTIBODIES TO ACTIVATED PLATELETS

[75] Inventors: Bruce E. Furie; Barbara C. Furie, both of Wellesley, Mass.

[73] Assignee: New England Medical Center Hospitals, Inc., Boston, Mass.

[21] Appl. No.: 796,621

[22] Filed: Nov. 8, 1985

Related U.S. Application Data

[63] Continuation-in-part of Ser. No. 671,759, Nov. 15, 1984, abandoned.

[51] Int. Cl.[4] ............... A61K 37/47; A61K 37/52; A61K 49/02; G01N 33/577
[52] U.S. Cl. .................................. 424/1.1; 424/9; 424/85.91; 424/94.63; 424/94.64; 435/172.2; 435/188; 435/240.27; 435/948; 436/519; 436/548; 530/387; 530/391; 530/808; 935/107; 935/110
[58] Field of Search ............... 435/7, 172.2, 240, 948, 435/27; 436/519, 548; 260/112 R; 935/95, 106, 107, 108, 110; 424/1.1, 9, 85, 94, 94.63, 94.64; 530/387, 391, 808

[56] References Cited

U.S. PATENT DOCUMENTS

| | | | |
|---|---|---|---|
| 4,486,538 | 12/1984 | Bogoch ............................ | 436/548 |
| 4,536,391 | 8/1985 | Miyazaki et al. .................. | 424/94 |
| 4,564,596 | 1/1986 | Maximenko et al. ............... | 424/94 |

OTHER PUBLICATIONS

S. B. Kadin et al., in J. J. Marchalonis et al. (Eds.) *Antibody as a Tool*, John Wiley & Sons, New York, 1982, pp. 457–460.
P. E. Stenberg et al., *Journ. Cell Biol.*, 101, 880–886, 1985.
Nieuwenhuis et al. (1983) Thromb. Haemostasis 50:100.
McEver et al. (1983) Blood 62, Suppl. 1, 262.
McEver et al. (1984) J. Biol. Chem. 259 (15):9799.
Hsu–Lin et al. (1984) Fed. Proc. 43, 3078B.
Hsu–Lin et al. (1984) Blood 62, Suppl. 1, 257.

*Primary Examiner*—Sidney Marantz
*Assistant Examiner*—David A. Saunders

[57] ABSTRACT

An antibody reactive with activated human platelets, and substantially unreactive with resting human platelets, with the azurophilic granules of monocytes, and with granulocytes.

18 Claims, 4 Drawing Sheets

The antibody bound to platelets is expressed in picomoles per $10^8$ platelets. ●, thrombin-activated platelets; ○, resting platelets.

B is the amount of antibody bound to platelets, expressed in picomoles per $10^8$ platelets. F is the free molar concentration of antibody.

●,▲, thrombin-activated platelets; ○,△, resting platelets. ○, CaCl₂; △, EDTA.

Resting platelets, ○; activated platelets, agonist: thrombin, ◇; ADP, △; epinephrine, ▽; collagen, □. Platelets were (○,◇,▽,□) or were not (●,◆,▲,▼,■) treated with acetylsalicylate. Platelet preparations that underwent aggregation are encircled.

MONOCLONAL ANTIBODIES TO ACTIVATED PLATELETS

BACKGROUND OF THE INVENTION

This invention was made in part with government support, and the government has rights in the invention.

This application is a continuation-in-part of U.S. patent application Ser. No. 671,759, filed Nov. 15, 1984 now abandoned.

This invention relates to antibodies, to diagnostic methods employing anibodies, and to blood platelets.

Platelets are anucleate cells which circulate in the blood in a resting, inactive form. During the initiation of hemostasis these cells are activated and undergo major functional changes which can be observed biochemically and morphologically. Studies comparing surface structures on resting and activated platelets have identified actin and an additional high molecular weight protein expressed on activated platelets. (George et al. (1980) J. Clin. Invest. 66, 1–9).

Niewenhuis et al. (1983) Thromb. Haemostasis 50, 100 describes a monoclonal antibody said to react with activated human platelets, azurophilic granules of granulocytes, and monocytes.

SUMMARY OF THE INVENTION

In general, the invention features, in one aspect, an antibody reactive with activated human platelets and substantially unreactive with reacting human platelets, and the azurophilic granules of monocytes and granulocytes.

Preferably the antibody recognizes an antigenic determinant on activated human platelets, the antigenic determinant being a glycoprotein distinct from glycoprotein IIa (glycoprotein IIa is a platelet surface antigen described, e.g., in Phillips et al. [1977] J. Biol. Chem. 252(6): 2121–2126).

The antibody is preferably of the IgG, most preferably IgG$_1$, isotype and recognizes an approximately 140,000 molecular weight glycoprotein antigenic determinant on the surface of activated platelets.

The antibody of the invention can be labeled with a detectable label, e.g. a radioactive label, a fluorophore, or a paramagnetic ion to form an NMR contrast agent, and used to detect activated platelet-containing sites in a human patient, in a method involving administering labeled antibody to the patient and detecting labeled immune complexes.

The antibody of the invention, because of its specificity for an antigenic determinant expressed only on activated, but not resting, platelets, can provide highly accurate information regarding the location of activated platelet-containing sites (e.g., thrombi) with very little background from resting platelets or other biological particles such as monocytes and granulocytes.

The antibody can also be used to assay a human blood sample for activated platelets, to yield diagnostically useful information.

All monoclonal antibodies having the above binding characteristics are encompassed by the present invention. These monoclonal antibodies are produced by hybrid cells made using conventional hybridization and screening techniques. As is well known in the monoclonal antibody field, each independently-produced hybrid cell line which produces a monoclonal antibody specific for the same antigenic determinant is nonetheless different from all others, as is each of the monoclonal antibodies so produced. Thus, while repetition of the procedure described herein will result in the production of a hybrid cell line which produces useful monoclonal antibody specific for the described antigenic determinant on activated platelets, it is highly unlikely that it will yield a cell line which produces a monoclonal antibody which is chemically an exact copy of the monoclonal antibody described below.

In addition to monoclonal antibodies, the invention encompasses polyclonal antibodies, particularly polyclonal antibodies raised by immunization of an animal with the purified 140,000 molecular weight glycoprotein antigenic determinant, above.

DESCRIPTION OF PREFERRED EMBODIMENT

We now describe preferred embodiments of the invention, after briefly describing the drawings.

Drawings

PREPARATION OF ACTIVATED PLATELETS

Figure 1:
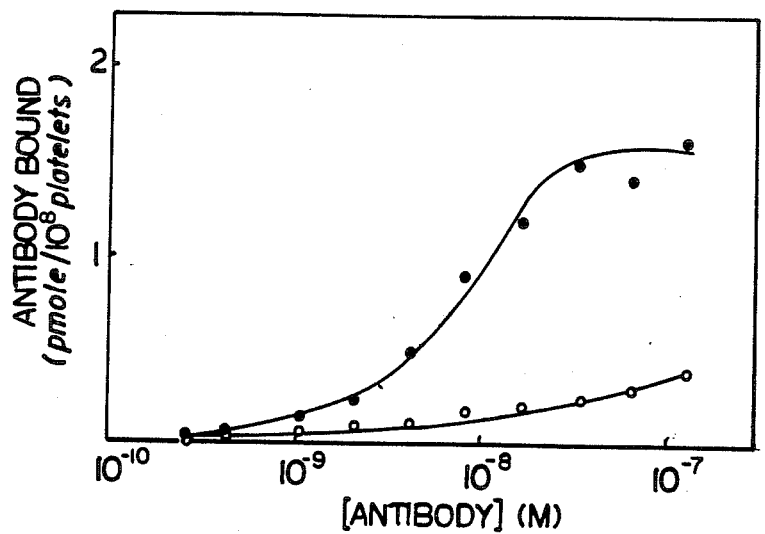
FIG. 1 is a graph showing the comparative interaction of an antibody of the invention with resting and activated platelets.

A monoclonal antibody of the invention was made as follows, beginning with the isolation of activated platelets.

Blood was obtained from normal human donors and anticoagulated with Ware's solution (0.1 M citrate buffer) at a 9:1 (v/v) ratio. Platelet-rich plasma (PRP), prepared by centrifugation of the citrated blood at 160×g for 15 min., was applied to a BSA discontinuous gradient, and the platelet concentrates were isolated. The platelets were further purified by gel filtration on a SEPHAROSE 2B (polysaccharide) column equilibrated with HEPES buffer, pH 7.35.

Thrombin-activated platelets were prepared by the addition of thrombin to a final concentration of 0.15 unit/ml to the gel-filtered platelet suspension and incubated without stirring for 2 min. Thrombin-activated platelets were fixed by the addition of 3% glutaraldehyde. The suspension was stirred slowly for 30 min., washed twice with TBS (20 mM Tris-HCl, 0.15 M NaCl, pH 7.5), and stored at −70° C. in 60% (v/v) glycerol.

Preparation of Anti-platelet Monoclonal Antibodies Specific for Activated Platelets Balb/c mice were immunized intraperitoneally with 1–5×10$^9$ thrombin-activated aggregated platelets suspended in 250 μl of HEPES buffer, pH 7.35. These mice were boosted with a similar platelet preparation from different donors biweekly for two months. The mice were rested for three months and a final boost was performed three days before cell fusion. The fusion was performed by the method described in Kohler and Milstein, Nature (1975) 256:495–497, using sp2/0 cells as a fusion partner. The supernatant medium from fused cells was assayed for anti-platelet antibody production. Selected positive cultures were cloned by the limiting dilution method described in McKearn, (1980) Monoclonal Antibodies (Kennett, R. H., McKearn, T. J., and Bechtol, K., eds) Plenum Press, New York, and a clone, designated "KC4", was isolated by carrying out an ELISA antibody screening procedure, as follows.

Glutaraldehyde-fixed thrombin-activated platelets or acetylsalicylate-treated resting platelets were suspended in TBS, pH 7.5, at a concentration of $1 \times 10^8$ platelets/ml. The platelet suspension (100 μl) was added to each MICROTITER (small well) (Immulon II, Dynatech Laboratories, Inc.) and centrifuged at 1000 g for 5 min. After the plates were washed with TBS, 200 μl of TBS with 0.5% gelatin and 50 μg/ml of human IgG were added and the plates incubated at 37° C. for 30 min. The MICROTITER (small well) wells were washed three times with TBS, and 100 μl of hybridoma culture supernatant were added and incubated at 37° C. for 1 hour. The MICROTITER (smalls well) wells were washed three times with TBS, 2 mM B-mercaptoethanol, 1.5 mM MgCl$_2$, and then 50 μl of sheep antimouse immunoglobulin conjugated with B-galactosidase (Bethesda Research Laboratories) were added and incubated at 22° C. for 2 hours. After washing three times with TBS, 2 mM B-mercaptoethanol, 100 μl of p-nitrophenyl B-D-galactoside (1 mg/ml) in 0.05 M sodium phosphate, 1.5 mM MgCl$_2$, pH 7.2, were added. The release of p-nitrophenol, as a measure of platelet-/antibody binding, was monitored over 30-60 minutes at 405 nm on a Dynatech MR580 MICROELISA Auto-Reader. The KC4 clone was isolated as producing antibody preferentially reactive with activated, compared to resting, platelets.

Hybrid cells of the KC4 clone, which produced anti-platelet antibody ("KC4 antibody"), were injected intraperitoneally into Balb/c mice. The ascites which developed was recovered and the KC4 antibody was isolated using Protein A-Sepharose affinity chromatography. The bound immunoglobulin was eluted by 0.1 M sodium citrate, pH 6.0. This antibody preparation yielded a single band in SDS gels under nonreducing conditions and two bands, corresponding to the heavy and light chain, in SDS gels under reducing conditions. The purified antibody was IgG$_1$k, as determined by Ouchterlony immunodiffusion using type-specific antisera.

Binding Specificity of KC4 Antibody

Purified KC4 monoclonal antibody was labeled with $^{125}$I using chloramine-T. The interactions of this antibody with unfixed gel-filtered thrombin-activated platelets and unfixed gel-filtered resting platelets were studied in a solution phase radioimmunoassay. As shown in FIG. 1, the monoclonal antibody displayed marked preference for the activated platelets. The interaction of KC4 antibody with thrombin-activated platelets was saturable. However, the binding of the KC4 antibody to resting platelets was minimal. Untreated platelets as well as platelets treated with adenosine and acetylsalicylate yielded equivalent results.

Figure 2:
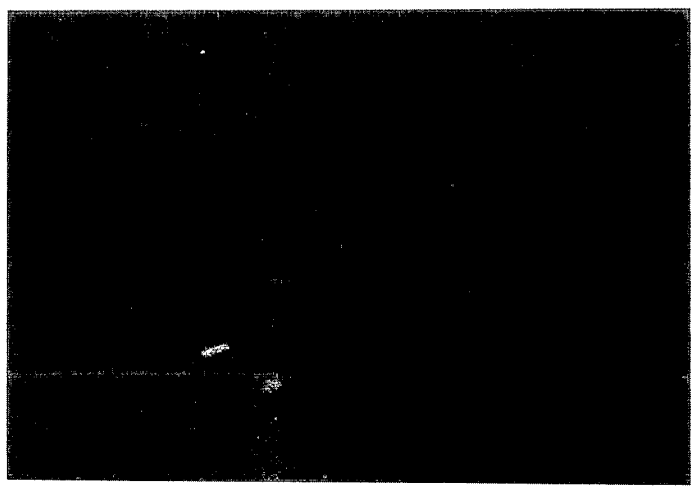
FIG. 2 is a pair of immunofluorescence photomicrographs illustrating the binding of an antibody of the invention to resting (A) and thrombin-activated (B) platelets.
Figure 2:
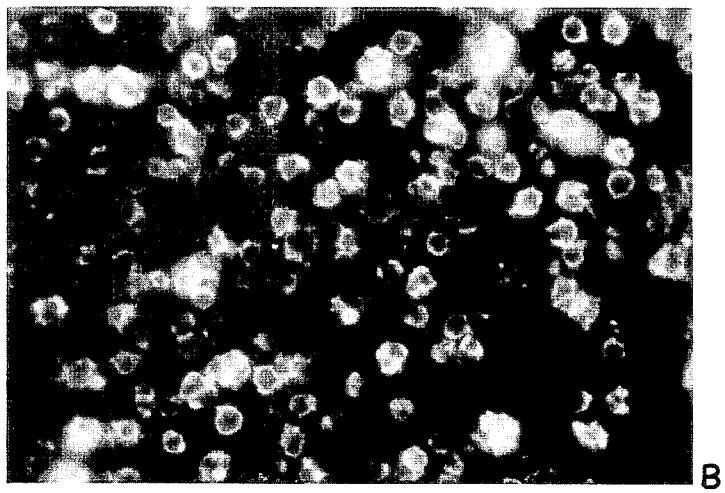

The preference of the monoclonal antibody for activated over resting platelets is also illustrated in the photomicrographs of FIG. 2. Binding of KC4 antibody to resting and thrombin activated platelets was detected using a fluorescence-labeled second antibody. As shown in FIG. 2, there was virtually no binding to resting platelets (panel A), compared to the binding to activated platelets (panel B).

Figure 3:
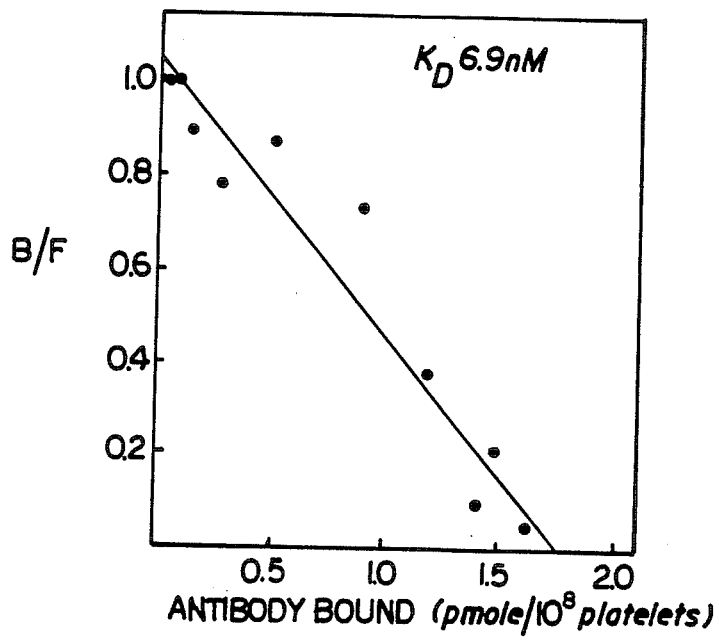
FIG. 3 is a graph of a Scatchard analysis of the interaction of an antibody of the invention with activated platelets.

The binding of KC4 antibody to thrombin-activated platelets was also evaluated using a Scatchard analysis. Using representative data from experiment 4 in Table I, below, a plot of the bound antibody concentration divided by the free antibody concentration versus the concentration of bound antibody yielded a straight line (FIG. 3). These results indicate a single class of antibody-binding sites on the platelet surface. Based on the analysis of this experiment, the binding constant, Kd, for the interaction of antibody with thrombin-activated platelets was 6.9 nM. Each platelet contained about 10,000-17,000 (in the case of this donor, 10,700) binding sites recognized by the KC4 antibody. These results further confirm the monoclonality of the antibody, manifested by homogeneity of the apparent binding constant measured.

The results of four independent experiments performed on platelets from four different donors are shown in Table I. There is excellent concordance of these data, with an average binding constant, $K_D$, of 7.2±0.4 nM. The average number of binding sites per platelet was 13,400±3,000.

TABLE I

Binding of KC4 monoclonal antibody to thrombin-activated platelets Each experiment includes assays performed in duplicate at 10 separate antibody concentrations. The antibody concentrations varied between $10^{-10}$ M and $2 \times 10^{-7}$ M.

| Experiment | $K_D$ nM | Binding sites/platelet | Correlation coefficient r |
|---|---|---|---|
| 1 | 7.4 | 16,374 | 0.93 |
| 2 | 7.5 | 12,160 | 0.95 |
| 3 | 6.8 | 14,087 | 0.96 |
| 4 | 6.9 | 10,716 | 0.96 |
| Average | 7.2 ± 0.4 | 13,400 ± 3,000 | |

Figure 4:
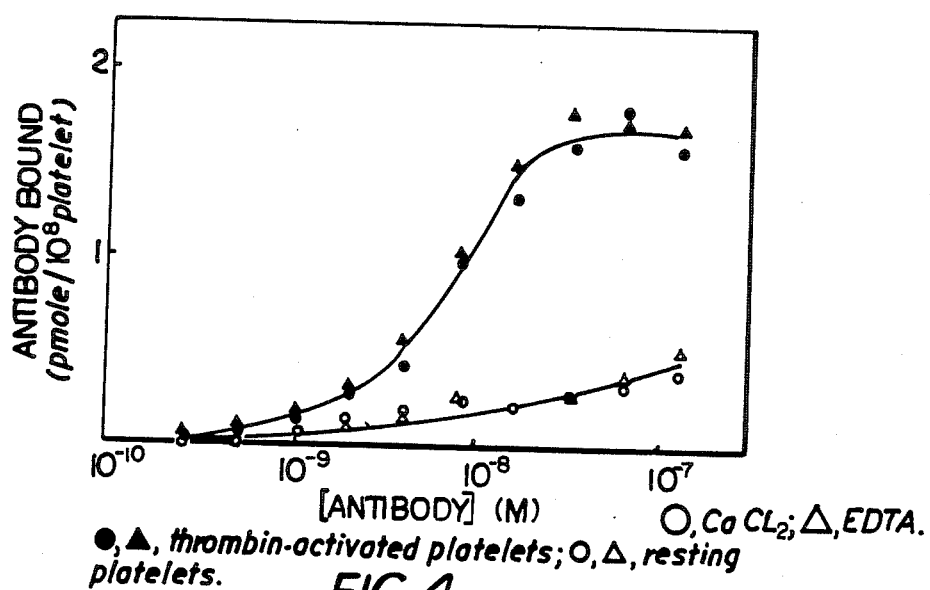
FIG. 4 is a graph illustrating the effects of calcium and EDTA on the binding of an antibody of the invention to activated and resting platelets.

Since platelet activation is associated with the secretion of proteins, such as thrombospondin, that bind to the plasma membrane in the presence of calcium ions, the effect of calcium or EDTA on KC4 antibody-platelet interaction was evaluated. As shown in FIG. 4, the binding curves of KC4 antibody-platelet interaction are unaltered by calcium ions or EDTA. These results indicate that the KC4 antibody is not directed against a platelet antigen whose antigenic structure is stabilized by metal ions nor is this antigen associated with the platelet surface through the action of metal ions. Furthermore, human plasma did not inhibit antibody binding to platelets, indicating that normal human plasma does not contain this platelet antigen. Buffers of high ionic strength (Tris buffer containing 1 M NaCl) or buffers with a pH from 4 to 10 did not alter the binding of the KC4 antibody to platelets.

Secretion-dependent Expression of the Platelet Antigen

The interactions of KC4 antibody with thrombin-activated platelets and platelets activated with other agonists were compared. In preliminary experiments, the KC4 antibody bond to platelets that were activated and aggregated with collagen, ADP, epinephrine, or thrombin (Table II). This interaction was also observed in unstirred thrombin-activated gel-filtered platelets which did not aggregate. Therefore, the binding of KC4 antibody to platelets appeared to be substantially independent of agonist and platelet aggregation.

TABLE II

| Binding of KC4 antibody to platelets activated by various agonists | |
|---|---|
| | Antibody bound |
| Thrombin (0.15 unit/ml) | 100 |
| ADP (10 μM) | 46 |
| Epinephrine (10 μM) | 66 |
| Collagen (0.45 mg/ml) | 72 |
| No agonist | 0 |

Figure 5:
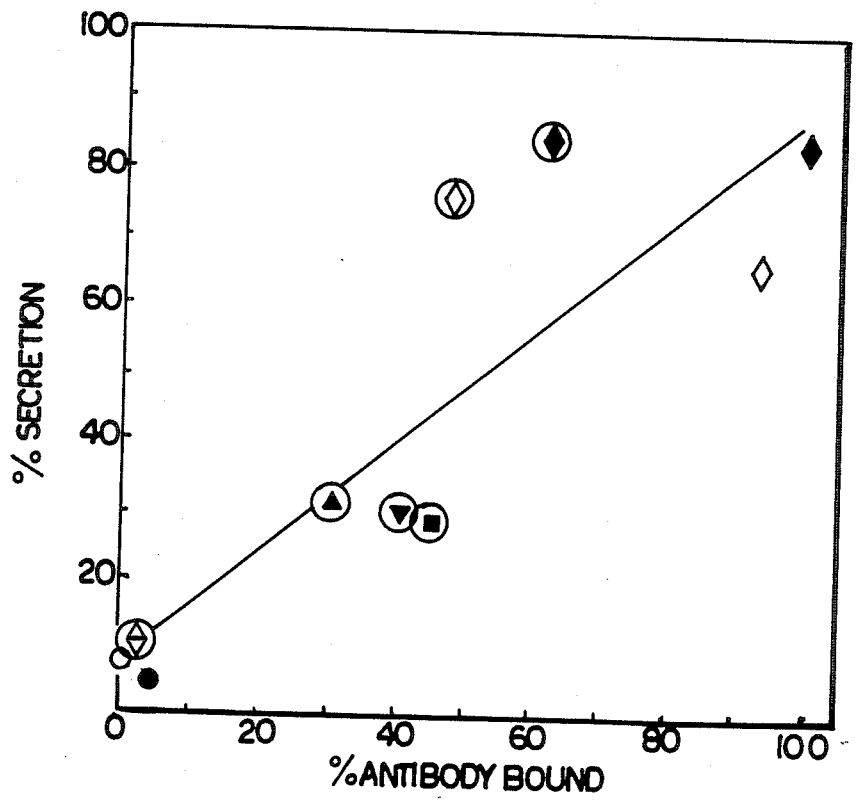
FIG. 5 is a graph illustrating the relationship between secretory function and activated platelet-specific antigen expression in activated platelets.

To evaluate whether the expression of the activated platelet-specific antigen was associated with secretion, platelets were loaded with [$^{14}$C] serotonin. The release of [$^{14}$C] serotonin from platelets upon activation by various agonists was compared to the binding of $^{125}$I-labeled KC4 antibody to these platelets. As shown in FIG. 5, antibody binding to the activated platelets correlated directly with secretion. Thrombin-activated platelets demonstrated maximal antibody binding and maximal secretion. Stimulation with ADP, epinephrine, or collagen resulted in lower levels of secretion and antibody binding. Platelets initially treated with acetylsalicylate (which impairs secretion) and activated with ADP, collagen, or epinephrine did not express the activation-specific antigen. These results suggest that the expression of the activation-specific antigen is secretion-dependent, but agonist- and aggregation-independent.

The activation-specific antigen is designated the "PADGEM" glycoprotein (for Platelet Activation-Dependent Granule to External Membrane). It is believed that the PADGEM glycoprotein exists as a part of an internal granule membrane in resting platelets, and that the PADGEM glycoprotein is exposed when, during activation and secretion, the granule membrane fuses with the external plasma membrane.

Antigen Specificity

The antigenic specificity of the KC4 antibody for a platelet antigen was determined using the Western blot method. Platelet proteins from platelets were solubilized in SDS and analyzed. The KC4 antibody bound to a single band in the solubilized platelets. This band migrated with an apparent molecular weight of 139,000. Platelets, surface-labeled with $^{125}$I using the lactoperoxidase method, were run for comparison. The characteristic band pattern of the $^{125}$I-labeled platelets showed GPIIb, GPIIa, and GPIII. The glycoprotein antigen of the KC4 antibody migrated between glycoproteins IIb and IIa and was distinct from them as well as distinct from glycoprotein III. Red blood cells, neutrophils, monocytes, lymphocytes, GM4672 (a lymphocytoid cell line), and Alexander PLC/PRF/5 (a human hepatoma cell line) were solubilized in SDS and their proteins similarly examined for binding to the KC4 antibody using the Western blot method. None of these cells contained proteins which bound to this antibody.

Purification of the PADGEM Glycoprotein

The PADGEM glycoprotein was purified from crude platelet membranes by affinity chromatography. The proteins were extracted from the membranes using Triton X-100, and these proteins applied to an affinity column containing the KC4 antibody covalently coupled to agarose. The material applied to the column was heterogeneous, and most of these proteins failed to bind to the KC4-agarose. The bound protein, eluted with diethylamine, migrated as a major diffuse band on SDS gels upon electrophoresis under nonreducing conditions, indicating substantial (greater than 80%) purity. The dominant protein band corresponded to an apparent molecular weight of 140,000. The character of this band was unchanged in the presence of Ca$^{++}$ or EDTA. In SDS gels run under reducing conditions, the purified PADGEM glycoprotein migrated as a single narrow band, also with a molecular weight of 140,000. These results indicate that the PADGEM glycoprotein is composed of a single polypeptide chain. The protein is stained with periodic acid-Schiff reagent, indicating that it is a glycoprotein.

Distinctiveness of PADGEM Glycoprotein

Figure 6:
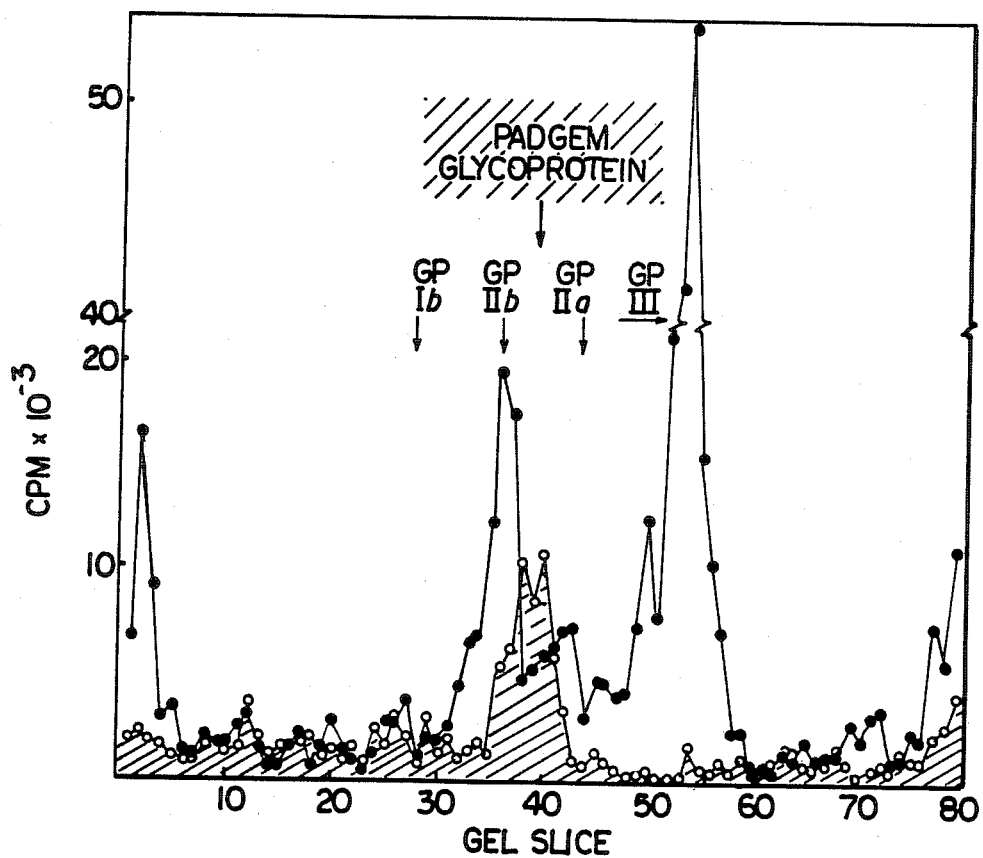
FIG. 6 is a gel electrophoresis graph showing that the antigen recognized by an antibody of the invention is distinct from glycoprotein IIa.

Referring to FIG. 6, the distinctiveness of the PADGEM glycoprotein from GPIIb and GPIIa was demonstrated using gel electrophoresis, as follows. Purified PADGEM glycoprotein was labeled with $^{125}$I to give $^{125}$I-labeled PADGEM glycoprotein. Resting platelets were labeled with $^{131}$I using the lactoperoxidase method to surface platelet membrane proteins, including GPIIb, GPIIa, and GPIII, with $^{131}$I. After treatment with sodium dodecyl sulfate, the $^{131}$I-labeled platelet glycoproteins (•) and the $^{125}$I-labeled PADGEM glycoprotein (o) were co-analyzed by gel electrophoresis. Padgem glycoprotein migrated between GPIIb and GPIIa, demonstrating its physical distinctiveness from GPIIa.

Padgem Glycoprotein Use

The PADGEM glycoprotein can be used as an immunogen to produce monoclonal antibodies of the invention. Production of antibodies using the PADGEM glycoprotein has the advantage, compared to the use of activated platelets as the immunogen, of producing only antibodies to the PADGEM glycoprotein, and not to antigens expressed on the surface of both activated and restin platelets. The PADGEM glycoprotein can also be used as an immunogen to produce polyclonal antibodies, which can be used in the in vitro assay described below.

The PADGEM glycoprotein has been used to immunize mice to produce monoclonal antibody-producing hybridoma cells with functional properties similar to those of KC4 antibody. A Balb/C mouse was immunized intraperitoneally once with 25 μg of PADGEM glycoprotein in complete Freund's adjuvant, and then twice, at two-week intervals, with 20 μg of PADGEM glycoprotein in saline. After an additional six-week period, mice were given a final boost with 20 μg PADGEM glycoprotein in saline, administered intravenously. A primary culture of these monoclonal antibody-producing cells has been deposited in the American Type Culture Collection, Rockville, Md. and given ATCC Accession No. HB 8670.

Applicants' assignee, New England Medical Center Hospital, acknowledges its responsibility to replace this culture should it die before the end of the term of a patent issued hereon, and its responsibility to notify the ATCC of the issuance of such a patent, at which time the deposit will be made available to the public. Until that time the deposit will be made available to the Commissioner of Patents under the terms of 37 CFR §1.14 and 35 USC §112.

As mentioned above, the PADGEM glycoprotein can also be used as an immunogen to produce monospecific polyclonal antibodies of the invention. Polyclonal anti-PADGEM protein antiserum was produced by immunization of a New Zealand white rabbit with 50 μg of purified PADGEM protein at monthly intervals. Antibodies specific for PADGEM protein were purfied on the PADGEM protein-Sepharase 4B column. The monospecificity of the purified anti-PADGEM protein polyclonal antobidies was established by the Western blot technique. The anti-PADGEM protein antibodies reacted with only a single protein in SDS-treated platelets, and were also found to react with purified PADGEM protein.

Antibody Use

The antibodies of the invention, because of their specificity for activated platelets, can be used to detect and localize activated platelets in vivo, particularly aggregates of immobilized activated platelets known to accumulate in thrombi resulting from vascular injury and disease, e.g., thrombosis, ischemic heart disease, gastric intestinal bleeding, and peripheral and cerebral vascular disease. Background and false positive results are avoided because the antibody not only fails to react with resting platelets, but also with other blood components such as granulocytes. The high binding affinity of the antibody provides good sensitivity.

The antibodies can be labeled using any conventional label, e.g., a radiolabel or a fluorophore. A preferred radiolabel is $^{111}$Indium, which has a half-life appropriate for defining platelet dynamics in humans. $^{111}$In-labeled antibodies can be prepared by modifying the antibody with diethylenediamine penta-acetic acid (DTPA) anhydride and subsequent chelation of '''Indium, according to the method described in Eckelman et al., 1975) Pharm. Sci., 64:704. It has been shown that '''Indium-labeled monoclonal and polyclonal antibodies bind to activated platelets in vitro.

To carry out in vivo imaging in the detection and localization of thrombi and activated platelets, a patient can be given an intravenous injection of approximately 500 uCi of sterile, pyrogen-free $^{111}$In-antibody in physiological saline. Whole body scan scinitigrams can then be taken using a gamma camera interfaced with a computer and fitted with a medium energy, parallel hole collimator and $^{111}$Indium images obtained about the $^{111}$Indium photopeaks.

The antibodies of the invention can also be labeled with a paramagnetic ion, e.g. $Gd^{+++}$ or $Mn^{++}$, to provide a targeted NMR contrast agent. The paramagnetic ion can be complexed with the antibody via a chelating agent such as DTPA using conventional techniques, e.g., the method described in Khaw et al. (1982) J. Nucl. Med. 23(11): 1011–1019. The contrast agent can be administered to a patient and NMR imaging carried out; the agents will provide NMR contrast between activated platelets, to which the targeted agents are bound, and other areas of the circulatory system.

A radiolabeled antibody of the invention can also be used to assay blood samples (preferably PRP) in vitro for activated platelets, as follows. Whole blood is collected in Ware's solution (described above) and centrifuged at 160×g for 12 minutes if derived from a female patient, 15 minutes if from a male, to obtain PRP. To 400 μl PRP in plastic tubes (in duplicate) is added 100 μl $^{125}$I-labeled KC4-antibody; to one tube, thrombin is simultaneously added to activate the platelets. The tubes are incubated at 23° C. for 15–20 minutes, and tube contents are then transferred to 1.5 ml microfuge tubes, with 400 μl Apiezon oil (9.3 parts n-butyl phthalate: 0.7 parts Apiezon).

The tubes are centrifuged in a Beckman ultracentrifuge for 3 minutes and then placed in a mixture of dry ice and acetone to freeze the pellets. The platelet-containing pellets are then cut off into plastic counting tubes and labeled immune complexes measured by counting the tubes in a gamma scintillation counter; a control sample of 100 μl $^{125}$I-labeled antibody is counted simultaneously.

Since the labeled antibody binds only to activated platelets, the above procedure provides a quantitative measure of activated platelets in blood samples. This information is diagnostically useful, circulating activated platelets being an indication that the patients blood is hypercoagulable (i.e., has an abnormally high tendency to clot) and the patient is in a potentially dangerous prethrombotic state.

In addition to being useful for localizing and characterizing activated platelets, in vivo imaging using labeled antibody of the invention can provide a sensitive means for evaluating the efficacy of thrombolytic agents, e.g., urokinase, streptokinase, and tissue plasminogen activator, in reducing the degree of myocardial necrosis following acute coranary thrombosis.

In addition, the antibody of the invention can be covalently bonded to a compound capable of dissolving an activated platelet-containing clot in a human patient. The compound can be one of the fibrin-lysing enzymes tissue plasminogen activator, streptokinase, urokinase, or plasmin. The specificty of the antibody targets the enzyme to the clot, increasing the specificity of the enzyme and thus reducing the dosage required, and reducing the risk of generalized fibrinolysis.

The antibody of the invention can be covalently bonded to a fibrinolytic enzyme such as urokinase generally as described in Bode et al. (1985) "Antibody-Directed Urokinase: A Specific Fibrinolytic Agent," Science 229,765, as follows. Reduced urokinase is coupled to the antibody by means of its intrinsic sulfhydryl groups, with N-succinimidyl 3-(2-pyridyldithio)propionate (SPDP) as a cross-linking agent. The cross-linking agent (20 mM in 0.05 ml of absolute ethanol) is added to the antibody [6.3 mg in 3.0 ml of phosphate-buffered saline (PBS) consisting of 0.1 M sodium phosphate and 0.1 M NaCl,pH7.4], and the mixture allowed to react for 30 minutes at room temperature. The solution is subsequently dialyzed three times against 1 liter of PBS.

The antibody-enzyme conjugate is injected, in a physiologically compatible carrier (such as saline) into a patient in need of blood clot lysis, in a dosage comparable to or lower than dosages ordinarily used for the unconjugated enzyme.

Other embodiments are within the following claims.

We claim:
1. A monoclonal antibody reactive with activated human platelets, and substantially unreactive with resting human platelets and with the azurophilic granules of monocytes and neutrophilic granulocytes.
2. The antibody of claim 1, said antibody being reactive with an antigenic determinant on the surfaces of activated human platelets and not present on the sur- faces of resting human platelets or azurophilic granules of monocytes, and neutrophilic granulocytes.

3. The antibody of claim 1, said antibody recognizing an antigenic determinant on activated human platelets, said antigenic determinant being a protein distinct from glycoprotein IIa.

4. The antibody of claim 1, said antibody being of the IgG isotype.

5. The antibody of claim 4, said antibody being of the IgG$_1$ isotype.

6. The antibody of claim 2, said antigenic determinant being a glycoprotein on the surface of activated platelets having a molecular weight of about 140,000.

7. The antibody of claim 1 said antibody recognizing between 10,000 and 17,000 binding sites on activated human platelets.

8. The antibody of claim 2, said antigenic determinant not being susceptible of stabilization, on activated human platelets, by calcium ions.

9. The antibody of claim 2, said antigenic determinant not being a constituent of normal human plasma.

10. The antibody of claim 1, the binding of said antibody to activated platelets being independent of platelet aggregation.

11. The antibody of claim 1, being labeled.

12. The antibody of claim 11, being radiolabeled.

13. The antibody of claim 11, complexed with a paramagnetic ion to form an NMR contrast agent.

14. A method of detecting activated platelet-containing sites in a human patient comprising administering to said patient the labeled antibody of claim 11 and detecting labeled immune complexes.

15. A method of assaying a platelet-containing sample for activated platelets comprising contacting said sample with the labeled antibody of claim 11 and measuring labeled immune complexes as a measure of said activated platelets in said sample.

16. A hybrid cell capable of producing the monoclonal antibody of claim 1.

17. The antibody of claim 1, being covalently bonded to a compound capable of dissolving an activated platelet-containing clot in a human patient.

18. The antibody of claim 17 wherein said clot-dissolving compound is tissue plasminogen activator, urokinase, streptokinase, or plasmin.

* * * * *